(12) United States Patent
Sacks et al.

(10) Patent No.: US 8,846,321 B2
(45) Date of Patent: Sep. 30, 2014

(54) ASSOCIATION OF LEVELS OF HDL-CHOLESTEROL APOLIPOPROTEIN CIII WITH THE RISK OF CORONARY HEART DISEASE AND CARDIOVASCULAR EVENTS

(75) Inventors: Frank M. Sacks, Belmont, MA (US);
Jeremy D. Furtado, Berkley, MA (US);
Eric Rimm, Brookline, MA (US);
Majken Jensen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/046,682

(22) Filed: Mar. 11, 2011

(65) Prior Publication Data

US 2011/0223158 A1  Sep. 15, 2011

Related U.S. Application Data

(60) Provisional application No. 61/313,700, filed on Mar. 12, 2010.

(51) Int. Cl.
*G01N 33/53* (2006.01)
*G01N 33/92* (2006.01)
*A61K 31/00* (2006.01)

(52) U.S. Cl.
CPC ............ *G01N 33/92* (2013.01); *G01N 2800/50* (2013.01); *G01N 2800/324* (2013.01); *A61K 31/00* (2013.01); *G01N 2800/52* (2013.01)
USPC .............................................. 435/7.1; 435/7.2

(58) Field of Classification Search
None
See application file for complete search history.

(56) References Cited

U.S. PATENT DOCUMENTS 7,098,036 B2 *  8/2006  Koren et al. .................... 436/71

OTHER PUBLICATIONS

Cohn et al. (J. Lipid Res 2003 vol. 44, p. 1976-1983).*
Nguyen et al. (J. Lipid Res. 2006 vol. 47, p. 1274-1280).*
Olivieri et al. (J Lipid Res 2003, vol. 44, p. 2374-2381).*
Onat et al. (Diabetic Medicine 2009 vol. 26, p. 981-988).*
Assmann et al., HDL cholesterol and protective factors in atherosclerosis. Circulation. Jun. 15, 2004;109(23 Suppl 1):III8-14.
Assmann et al., High-density lipoprotein cholesterol as a predictor of coronary heart disease risk. The PROCAM experience and pathophysiological implications for reverse cholesterol transport. Atherosclerosis. Jul. 1996;124 Suppl:S11-20.
Blankenhorn et al., Prediction of angiographic change in native human coronary arteries and aortocoronary bypass grafts. Lipid and nonlipid factors. Circulation. Feb. 1990;81(2):470-6.
Briel et al., Association between change in high density lipoprotein cholesterol and cardiovascular disease morbidity and mortality: systematic review and meta-regression analysis. BMJ. Feb. 16, 2009;338:b92.
Gordon et al., High density lipoprotein as a protective factor against coronary heart disease. The Framingham Study. Am J Med. May 1977;62(5):707-14.
Grundy et al., Implications of recent clinical trials for the National Cholesterol Education Program Adult Treatment Panel III Guidelines. J Am Coll Cardiol. Aug. 4, 2004;44(3):720-32.
Kawakami et al., Apolipoprotein CIII in apolipoprotein B lipoproteins enhances the adhesion of human monocytic cells to endothelial cells. Circulation. Feb. 7, 2006;113(5):691-700.
Onat et al., Apolipoprotein C-III, a strong discriminant of coronary risk in men and a determinant of the metabolic syndrome in both genders. Atherosclerosis. May 2003;168(1):81-9.
Sacks et al., VLDL, apolipoproteins B, CIII, and E, and risk of recurrent coronary events in the Cholesterol and Recurrent Events (CARE) trial. Circulation. Oct. 17, 2000;102(16):1886-92.
Sharrett et al., Coronary heart disease protection from lipoprotein cholesterol levels, triglycerides, lipoprotein(a), apolipoproteins A-I and B, and HDL density subfractions: The Atherosclerosis Risk in Communities (ARIC) Study. Circulation 2002; 104:1108-1113.
Singh et al., High-density lipoprotein as a therapeutic target: a systematic review. JAMA. Aug. 15, 2007;298(7):786-98.

\* cited by examiner

*Primary Examiner* — Jacob Cheu
(74) *Attorney, Agent, or Firm* — Wolf, Greenfield & Sacks, P.C.

(57) ABSTRACT

Presented herein are methods of diagnosing, assessing, and treating an individual at increased risk if developing coronary heart disease or cardiovascular event, based on the individual's level of high density lipoprotein cholesterol apoCIII (HDL-C apoCIII).

20 Claims, 1 Drawing Sheet

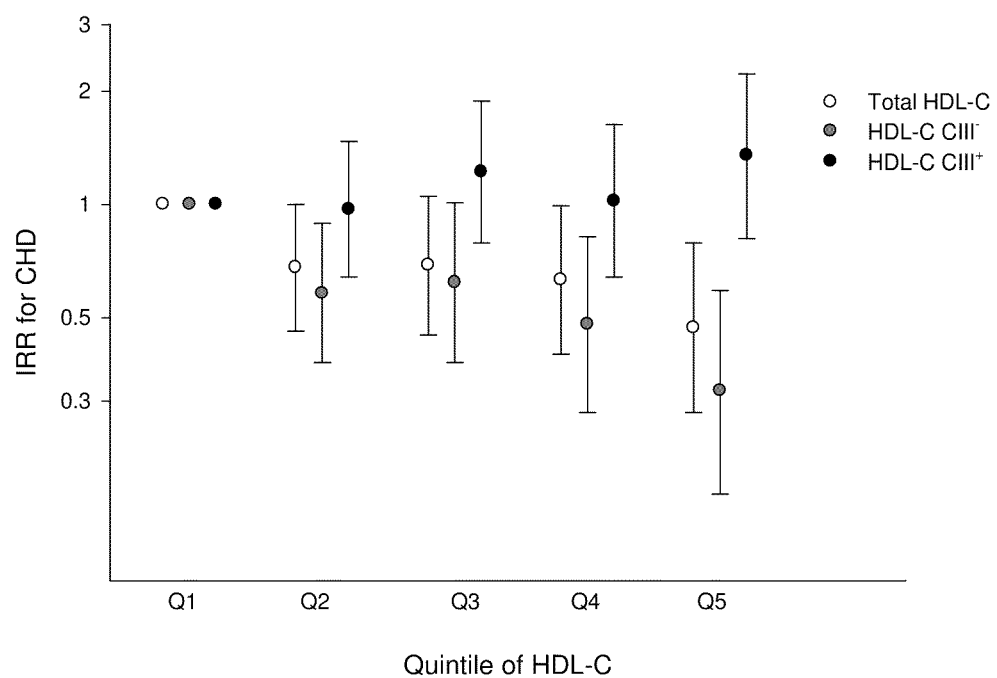

ASSOCIATION OF LEVELS OF HDL-CHOLESTEROL APOLIPOPROTEIN CIII WITH THE RISK OF CORONARY HEART DISEASE AND CARDIOVASCULAR EVENTS

RELATED APPLICATIONS

This application claims the benefit of U.S. provisional application No. 61/313,700, filed Mar. 12, 2010, the entire contents of which is herein incorporated by reference.

GOVERNMENT SUPPORT

This invention was made with government support under grants HL35464, AA11181, HL34594, and HL070159 awarded by the National Institutes of Health. The government has certain rights in the invention.

BACKGROUND

Population studies have shown that low-density lipoprotein cholesterol (LDL-C) is directly and high-density lipoprotein cholesterol (HDL-C) is inversely associated with the risk of coronary heart disease (CHD).[1-3] While statins and other classes of drugs efficiently reduce LDL-C and concomitantly lower the risk of cardiovascular events,[4] evidence for independent atheroprotective effects of HDL-C elevation is inconsistent.[5] The anti-atherogenic properties of an HDL particle include the ability to promote transport of cholesterol from peripheral tissues such as the artery wall to the liver as well as anti-inflammatory, anti-apoptotic, nitric oxide-promoting, prostacyclin-stabilizing, and platelet-inhibiting functions.[6] However, changes in HDL-C among all trials using hypolipidemic drugs did not independently predict changes in CHD; and the lack of CHD reduction in trials of a novel drug that raises HDL-C by an unprecedented amount suggests that the level of total circulating HDL-C is an insufficient measure of potentially cardioprotective HDL functions.[7-9] Metabolic heterogeneity of HDL particles may underlie the inconsistency between epidemiological studies, which consistently show independent risk prediction, and experimental approaches in clinical trials of lipid treatments. HDL comprises a diverse group of lipoproteins with substantial differences in size, density, and composition of lipids and proteins that influences the functional properties and metabolism of the particles.[10-12] Thus, it is likely that subpopulations of HDL with more or less anti-atherogenic potential can be identified. Although differential relations with risk of CVD have been observed for various HDL sub-group measures (e.g., particle size, various components, particle concentration, and anti-inflammatory properties), it remains inconclusive whether any of these techniques lead to potential gain in information in terms of CVD risk prediction.[13-18] Efforts to identify characteristics that may modulate the functional properties and metabolism of the HDL particle are important to improve the understanding of the atherosclerotic process and to prevent and treat cardiovascular diseases.

Previous work found that apolipoprotein (apo) CIII, a small pro-inflammatory protein that resides on the surface of some lipoproteins,[19,20] strongly increased the atherogenicity of VLDL and LDL,[21,22] and increased the prediction of risk.[23,24] Although HDL particles exist both with and without apoCIII, little is known about the role of apoCIII in relation to HDL function.

SUMMARY OF THE INVENTION

Described herein is a method of characterizing (assessing) an individual's risk of developing CHD or having a cardiovascular event, the method comprising (i) determining the level of high density lipoprotein cholesterol apoCIII (HDL-C apoCIII) in a sample obtained from the individual; (ii) comparing the level of HDL-C apoCIII in the sample to a predetermined value; and (iii) identifying the individual as at increased (greater or higher) risk of developing CHD or having a cardiovascular event if the level of HDL-C apoCIII in the sample is at (equal to) or above (greater than) the predetermined value. Also described is a method of characterizing an individual's risk of developing CHD or having a cardiovascular event, the method comprising (i) determining the level of HDL-C apoCIII in a sample obtained from the individual; (ii) comparing the level of HDL-C apoCIII in the sample to a predetermined value; and (iii) identifying the individual as at decreased (less or lower) risk of developing CHD or having a cardiovascular event if the level of HDL-C apoCIII in the sample is below (less than) the predetermined value. In this embodiment, if the individual's level of HDL-C apoCIII is at or above the predetermined value, he/she is at increased risk, relative to an individual whose HDL-C apoCIII level is below the predetermined level. If the individual's level of HDL-C apoCIII is below the predetermined value, he/she is at decreased risk, relative to an individual whose HDL-C apoCIII level is at or above the predetermined level. In specific embodiments, the predetermined value is an HDL-C apoCIII total blood plasma level of from about 2 mg/dl to about 12 mg/dl, such as about 2 mg/dl. Determining the level of HDL-C apoCIII in the sample can be carried out, for example, by measuring the level of HDL-C apoCIII in the sample, The sample that is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. Alternatively, they can have an above normal total blood plasma level of HDL-C. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of HDL-C that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

Also described herein is a method of evaluating the likelihood that an individual will benefit from treatment with an agent useful for reducing the risk of CHD or a cardiovascular event, the method comprising (i) determining the level of HDL-C apoCIII in a sample obtained from the individual; (ii) comparing the level of HDL-C apoCIII in the sample to a predetermined value; and (iii) identifying the individual as likely to benefit from treatment with the agent if the level of HDL-C apoCIII in the sample is at or above the predetermined value and as unlikely to benefit from treatment with the agent if the level of HDL-C apoCIII in the sample is below the predetermined value. Determining the level of HDL-C apoCIII in the sample can be carried out, for example, by measuring the level of HDL-C apoCIII in the sample.

The sample that is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. Alternatively, they can have an above normal total blood plasma level of HDL-C. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of apoCIII that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

Further described herein is a method of treating an individual to decrease (reduce or lower) the risk of developing CHD or having a future cardiovascular event, comprising (i) selecting the individual on the basis that the individual is known to have (has) a total blood plasma level HDL-C apoCIII above a predetermined value; and (ii) administering to the individual an agent useful for decreasing the risk of CHD or a cardiovascular event in an amount effective to decrease the individual's risk of developing a CHD or having a cardiovascular event.

Another embodiment described herein is a method of determining if a therapy is efficacious for decreasing an individual's risk of having a cardiovascular event, the method comprising (i) determining the level of HDL-C apoCIII in a sample obtained from an individual undergoing therapy with an agent useful for decreasing the risk of CHD or a cardiovascular event; (ii) comparing the level of HDL-C apoCIII in the sample to a predetermined value; and (iii) identifying the therapy as efficacious if the level is below the predetermined level and not efficacious if the level is at or above the predetermined level. Determining the level of HDL-C apoCIII in the sample can be carried out, for example, by measuring the level of HDL-C apoCIII in the sample. The cardiovascular event is, for example, myocardial infarction or stroke.

The sample in which the level of HDL-C apoCIII is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of HDL-C that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

Also described is a method of deciding on the course of (choosing or selecting) a therapy for an individual, comprising (i) obtaining (determining) a level of HDL-C apoCIII in a sample obtained from an individual, such as an individual undergoing a therapy to reduce the risk of developing CHD or having a cardiovascular event; (ii) comparing the level of HDL-C apoCIII obtained in the sample to a predetermined level of HDL-C apoCIII; (iii) determining whether the level of HDL-C apoCIII obtained in the sample is at or below the predetermined level; and (iv) deciding on the course of the therapy based on the determination, wherein if the level of HDL-C apoCIII is below the predetermined level, the therapy is continued (chosen or selected) and if the level of HDL-C apoCIII is at or below the predetermined level, the therapy is not continued (not chosen or selected). Determining the level of HDL-C apoCIII in the sample can be carried out, for example, by measuring the level of HDL-C apoCIII in the sample.

Further herein is a method of characterizing (assessing) an individual's risk of developing CHD or having a cardiovascular event, the method comprising (i) comparing the level of HDL-C apoCIII in a sample obtained from the individual to a predetermined value; and (ii) identifying the individual as at increased risk of developing CHD or having a cardiovascular event if the level of HDL-C apoCIII in the sample is at or above the predetermined value or as at decreased risk of developing CHD or having a cardiovascular event if the level of HDL-C apoCIII in the sample is below the predetermined value. In this embodiment, if the individual's level of HDL-C apoCIII is at or above the predetermined value, he/she is at increased (greater or higher) risk, relative to an individual whose HDL-C apoCIII level is below the predetermined level. If the individual's level of HDL-C apoCIII is below the predetermined value, he/she is at decreased (less or lower) risk, relative to an individual whose HDL-C apoCIII level is at or above the predetermined level. In specific embodiments, the predetermined value is an HDL-C apoCIII total blood plasma level of from about 2 mg/dl to about 12 mg/dl, such as about 2 mg/dl.

The sample that is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. Alternatively, they can have an above normal total blood plasma level of HDL-C. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of HDL-C that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

Also described herein is a method of evaluating the likelihood that an individual will benefit from treatment with an agent useful for decreasing the risk of CHD or a cardiovascular event, the method comprising (i) comparing the level of HDL-C apoCIII in a sample obtained from the individual to a predetermined value; and (ii) identifying the individual as likely to benefit from treatment with the agent if the level of HDL-C apoCIII in the sample is above the predetermined value and as unlikely to benefit from treatment with the agent if the level of HDL-C apoCIII in the sample is below the predetermined value.

The sample that is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. Alternatively, they can have an above normal total blood plasma level of HDL-C. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of HDL-C that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

In yet another embodiment described herein is a method of determining if a therapy is efficacious for decreasing an individual's risk of having a cardiovascular event, the method comprising (i) comparing the level of HDL-C apoCIII in a sample obtained from an individual undergoing therapy with an agent useful for decreasing the risk of CHD or a cardiovascular event to a predetermined value; and (ii) identifying the therapy as efficacious if the level is below the predetermined level and not efficacious if the level is at or above the predetermined level. The cardiovascular event is, for example, myocardial infarction or stroke.

The sample in which the level of HDL-C apoCIII is assessed is, for example, a blood sample obtained from the individual. Individuals assessed by a method described herein can have a total blood plasma level of apoCIII that is normal, such as a total blood plasma level of apoCIII of from about 2 mg/dl to about 24 mg/dl (e.g., 2 mg/dl, 4 mg/dl, 6 mg/dl, 8 mg/dl, 10 mg/dl, 12 mg/dl, 14 mg/dl, 16 mg/dl, 18 mg/dl, 20 mg/dl, 22 mg/dl, 24 mg/dl) or below normal. Individuals assessed by a method described herein can have a normal total blood plasma level of HDL-C, such as a total blood plasma level of HDL-C of from about 35 mg/dl to about 120 mg/dl. For example, in adult men, the total blood plasma level of HDL-C can be about 35 mg/dl or above and for adult women, the total blood plasma level of HDL-C can be about 45 mg/dl or above. Individuals assessed by the method can have a normal total blood plasma level of apoCIII (e.g., from about 2 mg/dl to about 24 mg/dl) or a total blood plasma level of apoCIII that is below normal and a normal total blood plasma level of HDL-C (e.g., from about 35 mg/dl to about 120 mg/dl) or a total blood plasma level of HDL-C that is above normal or any combination thereof (e.g., a normal total blood plasma level of apoCIII and a normal total blood plasma level of HDL-C; a normal total blood plasma level of apoCIII and a total blood plasma level of HDL-C that is below normal; a total blood plasma level of apoCIII that is below normal and a normal total blood plasma level of HDL-C; a total blood plasma level of apoCIII that is below normal and a total blood plasma level of HDL-C that is below normal; a normal total blood plasma level of apoCIII and a total blood plasma level of HDL-C that is above normal; a total blood plasma level of apoCIII that is below normal and a total blood plasma level of HDL-C that is above normal and other combinations). The cardiovascular event is, for example, myocardial infarction or stroke.

Also described is a method of deciding on the course of (choosing or selecting) a therapy for an individual, comprising (i) comparing the level of HDL-C apoCIII obtained from an individual undergoing a therapy to reduce the risk of developing CHD or having a cardiovascular event to a predetermined level of HDL-C apoCIII; (ii) determining whether the level of HDL-C apoCIII obtained in the sample is at or below the predetermined level; and (iii) deciding on the course of the therapy based on the determination, wherein if the level of HDL-C apoCIII is below the predetermined level, the therapy is continued (chosen or selected) and if the level of HDL-C apoCIII is at or above the predetermined level, the therapy is not continued (not chosen or selected).

BRIEF DESCRIPTION OF THE DRAWINGS

FIG. 1 is a graph showing the multivariable incidence rate ratio (IRR) for CHD according to quintiles of total HDL-C, without apoCIII (HDL-C CIII$^-$) and with apoCIII (HDL-CIII$^+$) in the Nurses' Health Study and Health Professionals Follow-Up Study based on the fully adjusted models. Multivariable model includes alcohol, BMI family history of MI before age 60, LDL-C and triglycerides, hypertension, and diabetes before blood draw. HDL-C with and without CIII simultaneously adjusted.

DETAILED DESCRIPTION OF THE INVENTION

The instant disclosure relates in part to a test for characterizing or assessing the risk of CHD or the risk of developing a future adverse cardiovascular event in an individual. This test also allows the determination of the likelihood that certain individuals will benefit from the use of certain treatments designed to prevent and/or treat cardiovascular disorders. The instant disclosure is based in part on the discovery that elevated levels of high density lipoprotein cholesterol apoCIII (HDL-C apoCIII) are predictive of future development of CHD or a cardiovascular event even after controlling for other factors such as, for example, obesity, hypertension, hyperlipidemia, and family history of cardiovascular disease. The predictive value of HDL-C apoCIII is independent of other predictors of CHD and adverse cardiovascular events.

This disclosure also relates in part to identifying individuals for treatment and to guide therapies based on measurement of HDL-C apoCIII.

In some embodiments, the individual does not have one or more of the following: obesity, diabetes mellitus, hypertension, family history of hypertension, previous adverse cardiovascular event(s), family cardiovascular disease or events (e.g., myocardial infarction (MI), history of smoking). In some embodiments, the individual is non-alcoholic.

In some embodiments the individual does not have one or more risk factor for CHD or a cardiovascular event. Examples of risk factors for CHD or a cardiovascular event include, but are not limited to, hypercholesterolemia (e.g., familial hypercholesterolemia), hypertriglyceridemia, mixed dyslipidemia, obesity, diabetes mellitus, hypertension, pre-hypertension, elevated level(s) of a marker of systemic inflammation (e.g., C reactive protein (CRP), sICAM-1, or sCD40), age, family history of cardiovascular events, and smoking. The degree of risk of a cardiovascular event depends on the multitude and the severity or the magnitude of the individual's risk factors. Risk charts and prediction algorithms are available for assessing the risk of cardiovascular events in an individual based on the presence and severity of risk factors. One such example is the Framingham Heart Study risk prediction score (Wilson et al., Circulation, 1998; 97:1837-1847). The human subject is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, or 20%.

Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging (MRI), and/or magnetic resonance angiography (Ridker et al., JAMA 297, 611, 2007).

In some embodiments the individual does not have clinical evidence of cardiovascular disease (e.g., coronary artery disease) or adverse cardiovascular events. In some embodiments the individual is an apparently healthy individual. An apparently healthy individual is an individual who has no signs and/or symptoms of a cardiovascular disease. A sign is an indication of the existence of an objective evidence of a disease, i.e., such evidence as is perceptible to the examining medical professional or health care provider. A symptom is a subjective evidence of disease or of an individual's condition, i.e., such evidence as perceived by the individual.

Examples of risk factors for CHD or a cardiovascular event include, but are not limited to, hypercholesterolemia, hypertriglyceridemia, mixed dyslipidemia, obesity, diabetes mellitus, hypertension, pre-hypertension, elevated level(s) of a marker of systemic inflammation (e.g., C reactive protein (CRP), sICAM-1, or sCD40), age, family history of cardiovascular events, and cigarette smoking. The degree of risk of a cardiovascular event depends on the multitude and the severity or the magnitude of the risk factors that the individual has. Risk charts and prediction algorithms are available for assessing the risk of cardiovascular events in an individual based on the presence and severity of risk factors. One such example is the Framingham Heart Study risk prediction score. The individual is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, or 20%.

Another method for assessing the risk of a cardiovascular event in an individual is a global risk score that incorporates a measurement of a level of a marker of systemic inflammation, such as CRP, into the Framingham Heart Study risk prediction score. Other methods of assessing the risk of a cardiovascular event in an individual include coronary calcium scanning, cardiac MRI, and/or magnetic resonance angiography (Ridker et al., JAMA 297, 611, 2007).

Examples of cardiovascular events, include, for example, myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

Hypercholesterolemic individuals and hypertriglyceridemic individuals have an increased risk of cardiovascular events. A hypercholesterolemic individual is one who fits the current criteria established for a hypercholesterolemic individual. A hypertriglyceridemic individual is one who fits current criteria established for a hypertriglyceridemic individual. In some embodiments, a hypercholesterolemic individual has a plasma LDL-C level of >160 mg/dl, or a plasma LDL-C level >130 mg/dl and at least two risk factors selected from the group consisting of: male gender, family history of premature CHD, cigarette smoking, hypertension, low plasma HDL-C (<35 mg/dl for men and <45 mg/dl for women), diabetes mellitus, hyperinsulinemia, abdominal obesity, high lipoprotein, and personal history of a cardiovascular event. In some embodiments, a hypertriglyceridemic individual has a plasma triglyceride (TG) level of >200 mg/dl. In some embodiments, a hypertriglyceridemic individual has a plasma triglyceride (TG) level of ≥225 mg/dl. In some embodiments, a hypertriglyceridemic individual has a plasma triglyceride (TG) level of ≥250 mg/dl.

A normal or desirable level of HDL-C is about 35 mg/dl or above for men and about 45 mg/dl or above for women. In some embodiments, an above-normal level of HDL-C is an HDL-C level is at least 10% more than the measured mean level for a given population of individuals. The mean HDL-C level can depend upon the particular population of individuals. In some embodiments, the HDL-C level is at least 10% more than the measured mean level for a given population of individuals. In other embodiments, the HDL-C level is at least 20% more than the measured mean level for a given population of individuals. In still other embodiments, the HDL-C level is at least 30%, 40%, 50%, 60%, 70%, 80%, 90%, 95%, 99% or 100% more than the measured mean level for a given population of individuals. In some embodiments, the level of HDL-C for men is about 40 mg/dl, 45 mg/dl, 50 mg/dl, 55 mg/dl, 60 mg/dl, 65 mg/dl, 70 mg/dl, 75 mg/dl, 80 mg/dl, 85 mg/dl, 90 mg/dl, 95 mg/dl, 100 mg/dl, 105 mg/dl, 110 mg/dl, 115 mg/dl, 120 mg/dl, 125 mg/dl, 130 mg/dl or above. In some embodiments, the level of HDL-C for women is about 50 mg/dl, 55 mg/dl, 60 mg/dl, 65 mg/dl, 70 mg/dl, 75 mg/dl, 80 mg/dl, 85 mg/dl, 90 mg/dl, 95 mg/dl, 100 mg/dl, 105 mg/dl, 110 mg/dl, 115 mg/dl, 120 mg/dl, 125 mg/dl, 130 mg/dl or above.

A below-normal level of apoCIII is a total plasma apoCIII level is at least 10% less than the measured mean level for a given population of individuals. The mean apoCIII level can depend upon the particular population of subjects. For example, an apparently healthy population will have a different "normal" range of apoCIII than will a population of individuals which have had a prior condition. In some embodiments, the apoCIII level is at least 10% less than the measured mean level for a given population of individuals. In other embodiments, the apoCIII level is at least 20% less than the measured mean level for a given population of individuals. In still other embodiments, the apoCIII level is at least 30%, 40%, 50%, 60%, 70%, 80%, 90%, 95%, 99% or 100% less than the measured mean level for a given population of individuals. In some of the embodiments, the total plasma apoCIII level is below about 24 mg/dl, 23 mg/dl, 22 mg/dl, 21 mg/dl, 20 mg/dl, 19 mg/dl, 18 mg/dl, 17 mg/dl, 16 mg/dl, 15 mg/dl, 14 mg/dl, 13 mg/dl, 12 mg/dl, 11 mg/dl, 10 mg/dl, 9 mg/dl, 8 mg/dl, 7 mg/dl, 6 mg/dl, 5 mg/dl, 4 mg/dl, 3 mg/dl, 2 mg/dl, 1 mg/dl. In some of the embodiments, the total plasma apoCIII level is undetectable.

Hypertension is a systolic blood pressure >120 mm Hg, and/or a diastolic pressure >80 mm Hg or both. Pre-hypertension is defined as systolic blood pressure between 115 and 120 mm Hg, and/or a diastolic pressure between 75 and 80 mm Hg.

Obesity is a state of excess adipose tissue mass. Although not a direct measure of adiposity, the most widely used method to gauge obesity is the body mass index (BMI), which is equal to weight/height$^2$ (in kg/m$^2$) (See, e.g., Harrison's Principles of Internal Medicine, 15th Edition, McGraw-Hill, Inc., N.Y.—hereinafter "Harrison's"). Based on data of substantial morbidity, a BMI of 30 is most commonly used as a threshold for obesity in both men and women. A BMI between 25 and 30 should be viewed as medically significant and worthy of therapeutic intervention, especially in the presence of risk factors that are influenced by adiposity, such as hypertension and glucose intolerance. Although often viewed as equivalent to increased body weight, this need not be the case. Lean but very muscular individuals may be overweight by arbitrary standards without having increased adiposity. Other approaches to quantifying obesity include anthropometry (skin-fold thickness), densitometry (underwater weighing), computed tomography (CT) or MRI, and/or electrical impedance.

Diabetes mellitus is established in an individual with a fasting plasma glucose level of 120 mg/dl or higher.

An elevated level(s) of a marker of systemic inflammation is a level that is above the average for a healthy human subject population. When the marker of systemic inflammation is CRP, in some embodiments a CRP level of ≥1 mg/dl is considered an elevated level. In other embodiments, a CRP level of ≥1.5 mg/dl is considered an elevated level. In yet other embodiments, a CRP level of ≥2 mg/dl is considered an elevated level.

Therapies for reducing the risk of a future cardiovascular event include but are not limited to diet and/or exercise and/or therapies with: anti-lipemic agents, agents that lower the levels of plasma apoCIII, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers and/or any combinations thereof.

Anti-lipemic agents are agents that reduce total cholesterol, reduce LDL-C, reduce triglycerides, and/or increase HDL-C. Anti-lipemic agents include statins and non-statin anti-lipemic agents, and/or combinations thereof. Statins are a class of medications that have been shown to be effective in lowering human total cholesterol, LDL-C and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDL-C uptake by liver cells. As LDL-C uptake is increased, total cholesterol and LDL-C levels in the blood decrease. Lower blood levels of both factors are associated with lower risk of atherosclerosis and heart disease, and the statins are widely used to reduce atherosclerotic morbidity and mortality.

Examples of statins include, but are not limited to, rosuvastatin (CRESTOR®), simvastatin (ZOCOR®), lovastatin (MEVACOR®), pravastatin (PRAVACHOL®), fluvastatin (LESCOL®), atorvastatin (LIPITOR®), cerivastatin (BAYCOL®), pitivastatin and numerous others described in U.S. Pat. Nos. 4,444,784, 4,231,938, 4,346,227, 4,739,073, 5,273,995, 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402.

Examples of statins already approved for use in humans include atorvastatin, cerivastatin, fluvastatin, pravastatin, simvastatin, and rosuvastatin. The reader is referred to the following references for further information on HMG-CoA reductase inhibitors: Drugs and Therapy Perspectives (May 12, 1997), 9: 1-6; Chong (1997) Pharmacotherapy 17:1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368. Another statin drug of note is compound 3a (S-4522) in Watanabe (1997) Bioorganic and Medicinal Chemistry 5: 437-444.

Non-statin anti-lipemic agents include, but are not limited to, fibric acid derivatives (fibrates), bile acid sequestrants or resins, nicotinic acid agents, cholesterol absorption inhibitors, acyl-coenzyme A, cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors, and peroxisome proliferation activated receptor (PPAR) agonists.

Examples of fibric acid derivatives include but are not limited to gemfibrozil (LOPID®), fenofibrate (TRICOR®), clofibrate (ATROMID®) and bezafibrate.

Examples of bile acid sequestrants or resins include but are not limited to colesevelam (WELCHOL®), cholestyramine (QUESTRAN® or PREVALITE®) and colestipol (COLESTID®), DMD-504, GT-102279, HBS-107 and S-8921.

Examples of nicotinic acid agents include but are not limited to niacin and probucol.

Examples of cholesterol absorption inhibitors include but are not limited to ezetimibe (ZETIA®).

Examples of ACAT inhibitors include but are not limited to Avasimibe, CI-976 (Parke Davis), CP-113818 (Pfizer), PD-138142-15 (Parke Davis), F1394, and numerous others described in U.S. Pat. Nos. 6,204,278, 6,165,984, 6,127,403, 6,063,806, 6,040,339, 5,880,147, 5,621,010, 5,597,835, 5,576,335, 5,321,031, 5,238,935, 5,180,717, 5,149,709, and 5,124,337.

Examples of CETP inhibitors include but are not limited to Torcetrapib, CP-529414, CETi-1, JTT-705, and numerous others described in U.S. Pat. Nos. 6,727,277, 6,723,753, 6,723,752, 6,710,089, 6,699,898, 6,696,472, 6,696,435, 6,683,099, 6,677,382, 6,677,380, 6,677,379, 6,677,375, 6,677,353, 6,677,341, 6,605,624, 6,586,448, 6,521,607, 6,482,862, 6,479,552, 6,476,075, 6,476,057, 6,462,092, 6,458,852, 6,458,851, 6,458,850, 6,458,849, 6,458,803, 6,455,519, 6,451,830, 6,451,823, 6,448,295, 5,512,548.

One example of an FXR antagonist is Guggulsterone. One example of a SCAP activator is GW532 (GlaxoSmithKline).

Examples of MTP inhibitors include, but are not limited to, Implitapide and R-103757.

Examples of squalene synthase inhibitors include, but are not limited to, zaragozic acids.

Examples of PPAR agonists include, but are not limited to, GW-409544, GW-501516, LY-510929, DRF 2519, (+)-Etomoxir sodium salt hydrate, GSK 3787, GW 0742, GW1929 hydrate, GW501516, L-165041, methyl-8-hydroxy-8-(2-pentyl-oxyphenyl)-oct-5-ynoate, nTZDpa, WY 14643 (ChemCruz™ Biochemicals), thiazolidinediones (e.g., pioglitazone (ACTOS®), rosiglitazone (AVANDIA®, and troglitazone (REZULIN®)), fibrates, muraglitazar, tesaglitazar, oleoyl ethanolamide. A PPAR agonist may agonize PPAR-$\alpha$, PPAR-$\beta$ (PPAR-$\delta$), or PPAR-$\gamma$, or other PPAR subtypes.

Agents that lower or regulate the level of apoCIII include statins (examples of statins are provided above); fibric acid derivatives (fibrates), including gemfibrozil, fenofibrate, ciprofibrate, and bezafibrate; dual alpha gamma PPARs; antisense drugs that inhibit apoB synthesis, including mipomersen; anti-apoCIII antisense products; fish oil or omega-3 fatty acid products, including LOVAZA®; insulin; and transcription factors HNF-4, ARP-1, EAR-2, EAR-3, PGC-1$\beta$, and NF-$\chi$B.

Anti-inflammatory agents include Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids, and Zomepirac Sodium.

Anti-thrombotic agents and/or fibrinolytic agents include tissue plasminogen activator (e.g., Activase, Alteplase) (catalyzes the conversion of inactive plasminogen to plasmin This may occur via interactions of prekallikrein, kininogens, Factors XII, XIIIa, plasminogen proactivator, and tissue plasminogen activator TPA) Streptokinase, Urokinase, Anisoylated Plasminogen-Streptokinase Activator Complex, Pro-Urokinase, (Pro-UK), rTPA (alteplase or activase; r denotes recombinant), rPro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, retaplase, Trifenagrel, Warfarin, Dextrans, aminocaproic acid (AMICAR®), and tranexamic acid (AMSTAT®).

Anti-platelet agents include Clopridogrel, Sulfinpyrazone, Aspirin, Dipyridamole, Clofibrate, Pyridinol Carbamate, PGE, Glucagon, Antiserotonin drugs, Caffeine, Theophyllin Pentoxifyllin, Ticlopidine, and Anagrelide.

Direct thrombin inhibitors include hirudin, hirugen, hirulog, agatroban, PPACK, and thrombin aptamers.

Glycoprotein IIb/IIIa receptor inhibitors are both antibodies and non-antibodies, and include but are not limited to abcixamab (REOPRO®), lamifiban, and tirofiban.

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-know in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also encompasses for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention encompasses polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids (e.g., poly-N-substituted glycines), peptidomimetics, and non-peptide synthetic moieties.

Examples of alpha-adrenergic blockers include: doxazocin, prazocin, tamsulosin, and tarazosin.

Beta-adrenergic receptor blocking agents are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, and 7-(2-hydroxy-3-t-butylaminpropoxy) phthalide. The above-identified compounds can be used as isomeric mixtures, or in their respective levorotating or dextrorotating form.

Cyclooxygenase-2 (COX-2) is a recently identified new form of a cyclooxygenase. Cyclooxygenase is an enzyme complex present in most tissues that produces various prostaglandins and thromboxanes from arachidonic acid. Nonsteroidal, antiinflammatory drugs exert most of their antiinflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It was originally identified in bovine seminal vesicles.

COX-2 has been cloned, sequenced and characterized initially from chicken, murine, and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the cyclooxygenase-1 (COX-1). COX-2, is rapidly and readily inducible by a number of agents including mitogens, endotoxin, hormones, cytokines and growth factors. As prostaglandins have both physiological and pathological roles, it is believed that the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar antiinflammatory, antipyretic and analgesic properties to a conventional non-steroidal antiinflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective COX-2 inhibitors are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2,3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; and U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid. Stability can be enhanced by other replacements that slow degeneration in vivo. Examples of angiotensin II receptor antagonists include but are not limited to: Candesartan (Alacand), Irbesartan (Avapro), Losartan (Cozaar), Telmisartan (Micardis), and Valsartan (Diovan). Other examples of angiotensin II antagonists include: peptidic compounds (e.g., saralasin, [(Sar$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c] pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D. Searle and Company).

Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Calcium channel blockers are a chemically diverse class of compounds having important therapeutic value in the control of a variety of diseases including several cardiovascular disorders, such as hypertension, angina, and cardiac arrhythmias (Fleckenstein, *Cir. Res. v.* 52, (suppl. 1), p. 13-16 (1983); Fleckenstein, *Experimental Facts and Therapeutic Prospects*, John Wiley, New York (1983); McCall, D., *Curr Pract Cardiol, v.* 10, p. 1-11 (1985)). Calcium channel blockers are a heterogenous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

Diuretics include but are not limited to: carbonic anhydrase inhibitors, loop diuretics, potassium-sparing diuretics, thiazides and related diuretics.

Vasodilators include but are not limited to coronary vasodilators and peripheral vasodilators, such as nitric oxide, noradrenaline, histamine, prostacyclin, prostaglandin $D_2$ and $E_2$, adenosine, L-arginine, platelet activating factor, $CO_2$, bradykinin, substance P, niacin, hydralazine (APRESOLINE®), minoxidil (ROGAINE®, REGAINE®, AVACOR®, LONITEN®, MINTOP®).

Vasopressors are agents that produce vasoconstriction and/or a rise in blood pressure. Vasopressors include but are not limited to: dopamine, ephedrine, epinephrine, Methoxamine HCl (Vasoxyl), phenylephrine, phenylephrine HCl (Neo-Synephrine), and Metaraminol.

Thiazolidinediones include but are not limited to: rosiglitazone (AVANDIA®), pioglitazone (ACTOS®), troglitazone (REZULIN®). Combination therapies of thiazolidinediones and other agents such as rosiglitazone and metformin (AVANDAMET®) are encompassed by this invention.

One example of a cannabinoid-1 receptor blocker is rimonabant.

The disclosure provides methods for determining whether an individual will benefit from continued therapy or would benefit from a change in therapy. The benefit is typically a reduction in the rate of occurrence of cardiovascular events. Determining whether an individual will benefit from continued therapy or would benefit from a change in therapy is clinically useful. One example of clinical usefulness of the methods of this invention includes identifying individuals who are less likely or more likely to respond to a therapy. The methods of the invention are also useful in predicting or determining that an individual would benefit from continued therapy or would benefit from a change in therapy. Another example of clinical usefulness includes aiding clinical investigators in the selection for clinical trials of human subjects with a high likelihood of obtaining a net benefit. It is expected that clinical investigators now will use the present invention for determining entry criteria for clinical trials.

An individual who would benefit from continued therapy is an individual whose on therapy level of HDL-C apoCIII reaches a certain predetermined value. Predetermined values of HDL-C apoCIII are described above. An individual who would benefit from a change in therapy is an individual whose on-therapy level of HDL-C apoCIII did not reach a certain predetermined value.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. In some embodiments, preferred therapies are therapies that lower levels of HDL-C apoCIII or apoCIII or both. An individual who would benefit from a change in therapy by increasing the dose of the existing therapy is an individual who, for example, was on the therapy but was not receiving the maximum tolerated dose or the maximum allowed dose of the therapy and whose level of HDL-C apoCIII did not reach a certain predetermined value. In such instances the dose of the existing therapy is increased until the level of HDL-C apoCIII reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. An individual who would benefit from a change in therapy by decreasing the dose of the existing therapy is, for example, an individual whose on therapy level of HDL-C apoCIII reaches or can reach a certain predetermined value with a lower dose of the therapy.

An individual who would benefit from a switch from one therapy to another therapy is, for example, an individual who was on the maximum tolerated dose or the maximum allowed dose of the therapy and whose level of HDL-C apoCIII did not reach a certain predetermined value. Another example is a an individual was not on the maximum tolerated or the maximum allowed dose of the therapy but was determined by a health care practitioner to more likely benefit from another therapy. Such determinations are based, for example, on the development in the individual of unwanted side effects on the initial therapy or a lack of response to the initial therapy.

An individual who would benefit from a change in therapy by the addition of another therapy to the existing therapy is, for example, an individual who was on a therapy but whose level of HDL-C apoCIII did not reach a certain predetermined value. In such instances, another therapy is added to the existing therapy. The therapy that is added to the existing therapy can have a different mechanism of action in lowering the level of HDL-C apoCIII than the existing therapy. In some instances, a combination of the aforementioned changes in therapy may be used.

The disclosure also provides methods for determining the efficacy of a therapy. The efficacy is typically the efficacy of the therapy in lowering the level of HDL-C apoCIII. This is sometimes also referred to as a positive response or a favorable response. Efficacy can be determined by a HDL-C apoCIII blood test(s) to determine whether HDL-C apoCIII levels are lowered as a result of therapy. In some embodiments efficacy determination is based on the efficacy of a therapy in lowering both HDL-C apoCIII and lipid levels (e.g., cholesterol or LDL-C).

The disclosure also provides methods for deciding on the course of a therapy in an individual undergoing therapy to reduce the risk of a future adverse cardiovascular event. Such a course of therapy is decided on the basis of the level of HDL-C apoCIII. Therapies for reducing the risk of future cardiovascular events are described above. In some embodiments, the individual already has had a cardiovascular event, such as, for example, a myocardial infarct or has had an angioplasty. An individual who has had a primary (first) cardiovascular event is at an elevated risk of a secondary (second) cardiovascular event due to the primary cardiovascular event. In some embodiments, the individual is at an elevated risk of a cardiovascular event because the individual has one or more risk factors to have a cardiovascular event. Examples of risk factors to have a cardiovascular event are described above. In some embodiments, the individual who is at an elevated risk of a cardiovascular event may be an apparently healthy human individual.

These methods have important implications for patient treatment and also for the clinical development of new therapies. It is also expected that clinical investigators now will use the present methods for determining entry criteria for individuals in clinical trials. Health care practitioners select therapeutic regimens for treatment based upon the expected net benefit to the individual. The net benefit is derived from the risk to benefit ratio. The present invention permits the determination of whether an individual will benefit from continued therapy or would benefit from a change in therapy, thereby aiding the physician in selecting a therapy.

When a therapeutic agent is administered, it is administered in an amount effective to reduce the risk of coronary artery disease or a future cardiovascular event. An effective amount is a dosage of the therapeutic agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. For example, an effective amount can depend upon the degree to which an individual has elevated levels of HDL-C apoCIII. It should be understood that the therapeutic agents of the invention are used to reduce (partially or totally) the severity or the manifestation of the cardiovascular events, that is, they are used prophylactically in human subjects at risk of developing a cardiovascular event. Thus, an effective amount is that amount which can lower the risk of, slow or perhaps prevent altogether the development of a cardiovascular event. It will be recognized when the therapeutic agent is used in acute circumstances, it is used to reduce (partially or totally) one or more medically undesirable results that typically flow from such adverse events. In the case of myocardial infarction, the therapeutic agent can be used to limit injury to the cardiovascular tissue which develops as a result of the myocardial infarction and in the case of restenosis, the therapeutic agent can be used in amounts effective to inhibit, prevent or slow the reoccurrence of blockage.

Generally, doses of active compounds or agents would be from about 0.01 mg/kg per day to 1000 mg/kg per day. It is expected that doses ranging from 50-500 mg/kg will be suitable, preferably orally and in one or several administrations per day. Lower doses will result from other forms of administration, such as intravenous administration. In the event that a response in a human subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The therapeutic agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human subject. The term "carrier" denotes an organic or inorganic ingredient, natural or synthetic, with which the active ingredient is combined to facilitate the application. The components of the pharmaceutical compositions also are capable of being co-mingled with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the therapeutic agent, which is preferably isotonic with the blood of the subject. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular therapeutic agent selected, the severity of the condition being treated and the dosage required for therapeutic efficacy. The methods of the invention, generally speaking, may be practiced using any mode of administration that is medically acceptable, meaning any mode that produces effective levels of the active compounds or agents without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the therapeutic agent into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the therapeutic agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the therapeutic agent, increasing convenience to the subject and the health care practitioner. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the therapeutic agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for therapy of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

In some embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

The cardioprotective benefits of elevated high-density lipoprotein cholesterol (HDL-C) levels are up for debate. HDL are metabolically heterogeneous particles that could have differential effects in atherosclerosis. We investigated whether apolipoprotein (apo) CIII, a small pro-inflammatory protein residing on the surface of lipoproteins, influences the association between HDL-C and risk of CHD.

The cholesterol concentration in HDL (HDL-C) was measured in plasma separated by presence or absence of apoCIII (CIII$^+$ or CH$^{1-}$) in 632 CHD cases and matching controls from parallel prospective nested case-control studies in women and men.

Level of HDL-C CIII$^+$ was directly associated with risk of CHD (incidence rate ratio [IRR] per 3.76 mg/dl~1 sd=1.27, 95% CI: 1.06-1.52). In contrast, an inverse association with CHD was observed for HDL-C CII$^-$ (IRR=0.63, 0.50-0.79, per 20.7), even stronger than that for total HDL-C (IRR=0.76, 0.62-0.92, per 22.8 mg/dl). HDL-C CIII+ comprised ~13% of the total HDL-C. Women had higher levels of both types of HDL-C than men, but associations were similar across gender. Participants with high concentrations of HDL-C CIII+ had higher triglycerides and LDL-C. Further adjustment for these lipids attenuated the results, however the HDL-C with and without apoCIII remained differentially associated with risk of CHD (p for slope heterogeneity=0.02). The concentration of apoCIII in HDL was not statistically significantly associated with risk of CHD.

Presence of apoCIII may indicate a dysfunctional subpopulation of HDL without cardioprotective benefits and separate measures of HDL with and without apoCIII may better discriminate future risk of CHD than total HDL.

Methods

Study population: The Nurses' Health Study (NHS) enrolled 121,701 female nurses aged 30 to 55 who returned a mailed questionnaire in 1976 regarding lifestyle and medical history. The Health Professionals Follow-up Study (HPFS) enrolled 51,529 males aged 35 to 75 who returned a similar questionnaire in 1986. Participants of both cohorts have received follow-up questionnaires biennially to record newly diagnosed illnesses and to update lifestyle and dietary information. Detailed descriptions of the study cohorts have been published previously.[25,26] Between 1989 and 1990, a blood sample was requested from all active participants in NHS and collected from 32,826 women, similarly, blood samples were requested between 1993 and 1995 and obtained from 18,225 HPFS participants.

In both cohorts, nested case-control studies were designed using incident CHD, with non-fatal MI and fatal CHD as the outcome. Among participants who provided blood samples and who were free of diagnosed cardiovascular disease or cancer at blood draw, we identified 474 women and 454 men with incident CHD between blood draw and June, 2004. Using risk-set sampling,[27] controls were selected randomly and matched in a 1:1 ratio on age, smoking, and month of blood return, among participants who were free of cardiovascular disease at the time CHD was diagnosed in the case. Because the complete laboratory measurements required a large volume (0.600 ml) we were not able to obtain sufficient plasma from all participants. See details about exclusions below.

Assessment of coronary heart disease: Diagnosis of myocardial infarction was confirmed on the basis of the criteria of the World Health Organization (symptoms plus either diagnostic electrocardiographic changes or elevated levels of cardiac enzymes). Deaths were identified from state vital records and the National Death Index or reported by the participant's next of kin or the postal system. Fatal CHD was confirmed by an examination of hospital or autopsy records, by the listing of CHD as the cause of death on the death certificate, if CHD was the underlying and most plausible cause, and if evidence of previous CHD was available.

Biochemical measurements: Blood samples were collected in tubes treated with liquid sodium heparin (in NHS) or EDTA (in HPFS). The tubes were then placed on ice packs, stored in Styrofoam™ containers, returned to our laboratory by overnight courier, centrifuged, and divided into aliquots for storage in liquid-nitrogen freezers (−130° C. or colder) Immuno-affinity chromatography was conducted with affinity-purified anti-human apoCIII to separate the plasma into fractions with (CIII$^+$) and without (CIII$^-$) apoCIII. Detailed methods have been published previously.[28] Subsequently, apoCIII-bound and -unbound fractions were ultracentrifuged to isolate the very low-density (d<1.006 g/mL), low-density (1.006<d<1.063 g/mL) and high-density (d>1.063 g/mL) lipoprotein particles. ApoCIII and cholesterol in both fractions of HDL was determined by ELISA. Detailed methods have been published previously[28] and briefly below.

Each batch in a laboratory analysis included the matched case-control sets so that run-to-run variation in the analysis would not add imprecision to the differences between cases and controls. All laboratory personnel were blinded to the case-control status. The within-run average CVs were 8% for HDL-C CIII$^-$, 13% for HDL-C CIII$^+$, and 17% for apoCIII in HDL.

A small fraction of the cholesterol in the d>1.063 fraction prepared by ultracentrifugation could be transported in very dense LDL particles co-isolated with HDL. Sufficient plasma volumes were available in the HPFS to repeat the measurement of cholesterol in HDL CIII+ and CIII− after precipitation of apoB lipoproteins by dextran sulfate and magnesium chloride. In the NHS this direct measurement was only possible in a subsample of 24 women with sufficient plasma left. We used this subset with both cholesterol measures in addition to measurements of the apoB concentration to estimate the average cholesterol per apoB particle in the d>1.063 fraction. Subsequently we computed the HDL-C measures for the NHS cohort by subtracting the cholesterol that was associated with very dense LDL in each of the apoC compartments. The proportion of cholesterol that was estimated to be associated with apoB particles in the d>1.063 fraction was 0.68 mg/dL in the apoC$^+$ fraction and 0.79 mg/dL in the apoC$^-$ fraction.

The study protocol was approved by the institutional review board of the Brigham and Women's Hospital and the Human Subjects Committee Review Board of Harvard School of Public Health.

Immuno-affinity chromatography: Samples are removed from cryogenic storage and thawed, preferably in the dark at room temperature for 30 min Samples are filtered, and 700 µL filtered plasma is loaded into 20 mL Econo-Pac columns (Bio-Rad Laboratories, Hercules, Calif.) packed with anti-apo C-III resin (polyclonal goat anti-human apo C-III antibody bound to Sepharose 4B Resin; Academy Biomedical Company Inc, Houston, Tex.). Samples and resin are incubated for 16 h at 4° C. with mixing. The unbound fraction is eluted from the column by gravity followed by washes with phosphate-buffered saline. The bound fraction is then eluted from the columns with 3 mol/L sodium thiocyanate in phosphate-buffered saline and is immediately desalted with the use of PD-10 columns (GE Healthcare, Little Chalfont, United Kingdom).

The immunoaffinity columns consists of 2.5 mL anti-apo C-III resin prepared with the use of polyclonal goat anti-human apo C-III antibody bound to Sepharose 4B Resin at a minimum concentration of 5 mg antibody/mL resin. All columns are tested to ensure efficiency of >95% before the start of laboratory analysis and midway through the analysis period by application of a quality control plasma sample to each column and measurement of apo C-III concentration of both the retained and unretained fractions. In addition, a separate quality control sample is included in each sample batch that was randomly assigned to a different column.

Ultracentrifugation: The bound and unbound fractions are ultracentrifuged to separate particles by density. VLDL are isolated by overlaying 700 µl of sample with 300 µl of potassium bromide [with density (d)=1.006 g/ml] aqueous solution (Sigma-Aldrich, St. Louis, Mo.) and spinning for 16 h at 15° C. and 25 000 rpm in the outer-most row of a Beckman 25-Ti rotor with a Beckman L8-70 M ultracentrifuge (Beckman Coulter, Inc, Fullerton, Calif.). The top 200±10 µl from each tube are collected by careful aspiration and stored at 4° C. briefly, pending same-day analysis of lipids and apolipoproteins while the next ultracentrifugation step for LDL is prepared. LDL is isolated by overlaying the plasma remaining after VLDL aspiration with 34% potassium bromide solution to produce a final density of 1.063 g/ml and spinning for 24 h under the same conditions as for VLDL isolation. The top 300±10 µl from each is collected by aspiration. Three density fractions of plasma are thus isolated: <1.006 g/ml (VLDL), 1.006 g/ml to <1.063 g/mL (LDL), and >1.063 g/ml (HDL and very dense LDL).

Determination of lipids and apolipoproteins: Sandwich enzyme-linked immunoabsorbent assay (ELISA) procedures with the use of affinity-purified antibodies (Academy Biomedical Company Inc) are performed to determine the concentrations of apo B, apo C-III, and apolipoprotein E (apo E) in whole plasma and the lipoprotein fractions. TGs and cholesterol are determined enzymatically (Thermo Scientific, Waltham, Mass.). Liquid transfer for 96-well plate loading and ELISA dilutions are handled robotically with a Multiprobe II (Perkin-Elmer, Waltham, Mass.) to minimize pipetting error. Both ELISA and lipid plates are read with a BioTek ELx808iu 96-well plate reader controlled by KCJUNIOR software (BioTek, Winooski, Vt.). All assays are completed in triplicate, and any sample with an intraassay CV>15% is repeated.

Assessment of other variables: Anthropometric, lifestyle, and dietary data were derived from questionnaires administered at blood draw (1990 in the NHS and 1994 in the HPFS), with missing information substituted from previous questionnaires Body-mass index (BMI) was calculated as the weight in kilograms divided by the square of the height in meters. Physical activity was expressed in terms of metabolic equivalent (MET)-hours. Participants reported whether a physician had ever diagnosed them with diabetes or hypertension. The questionnaires and the validity and reproducibility of measurements have been described previously.[26]

Exclusions and missing data: Due to limited plasma volumes not all participants were measured and for this analysis. Matched case-control sets with missing data on the measures of HDL-C in either the case or the control were excluded. After additional exclusion of 22 participants identified as outliers based on ±3 IQR, our final data sets consisted of 568 women (284 case-control sets) and 697 men (348 case-control sets).

Statistical analysis: Means and proportions of lifestyle and lipid concentrations were calculated in controls and participants who developed CHD during follow-up. Age-standardized means of characteristics and tests of trend were calculated according to quintiles of HDL-C CIII$^+$ and CIII$^-$. Relative risks (RR) and 95% confidence intervals (CIs) for CHD-risk were estimated by the incidence rate ratios from conditional logistic regression analyses taking into account the matching factors (sex, age, and batch).[27] In primary analyses we used splines to visualize and test for a linear association between the lipid parameters and risk of CHD. We found no violations of the linear assumptions and subsequently analyzed the RR according to 1 standard deviation (SD) difference in the HDL-C measures (22.8 mg/dl HDL-C, 20.7 mg/dl HDL-C CIII$^-$, and 3.76 mg/dl HDL-C CIII$^+$ in the combined controls). There was no evidence of heterogeneity of the associations between men and women. We also created cohort-specific quintiles for the lipid parameters using the distributions in the controls. Multivariable analyses included adjustment for alcohol, BMI, hypertension, and family history of MI before age 60. Additional adjustment for physical activity did not impact the results. Further adjustments included measures of LDL-C and triglycerides (both entered in quintiles) and information on self-reported diabetes.

In sensitivity analyses, we repeated our analyses after exclusion of participants who reported taking cholesterol lowering drugs at baseline (total of 89 individuals). These results were not appreciably different from the main results reported here (data not shown). Additionally we compared the associations from analyses in strata of 5 years of follow-up. Analyses were performed using SAS 9 (SAS Institute Inc., Cary, N.C.).

Baseline characteristics: As expected, participants who developed CHD during follow-up had had lower levels of HDL-C than controls (Table 1). The majority of HDL-C was without apoCIII, with a higher proportion in women compared to men (mean HDL-C with apoCIII was 14.4% in women and 10.0% in men). The concentration of HDL-C CIII$^+$ and CIII$^-$ in women were 9.46 and 60.9, respectively, and 5.40 and 42.4 mg/dL in men. The proportion was slightly higher in cases compared to controls in both genders.

Participants with high concentration of HDL-C CIII$^-$ were less likely to have diabetes or hypertension at baseline, had higher alcohol intake, higher levels of physical activity, and lower triglycerides, LDL-C, BMI and carbohydrate intake. In contrast, high levels of HDL-C CIII+ was associated with also higher triglycerides level in both genders, but with higher alcohol intake, levels of LDL-C, prevalent diabetes, and lower carbohydrate intake in men only (Table 2).

HDL-C with and without apoCIII and risk of coronary heart disease: Higher levels of HDL-C CIII$^+$ was associated with an increased risk of CHD. In multivariable-adjusted models without other lipid risk factors, each SD increase (3.76 mg/dL) was associated with a 27% higher risk of CHD. In contrast, HDL-C CIII$^-$ predicted a lower risk of CHD (Incidence rate ratio [MR] IRR=0.63, 95% CI; 0.50-0.79, per 20.7 mg/dL~1 SD), even stronger than that for total HDL-C (IRR=0.76; 0.62-0.92, per 22.8 mg/dL) (Table 3). The slopes of the regression coefficients for the two HDL-C subfractions were statistically significantly different (p=0.002). Although we did not detect any interaction with gender the associations appeared slightly stronger in the women than the men (Table 3). Additional adjustment for LDL-C and triglycerides attenuated the RR's but the test of slope heterogeneity remained statistically significant (p=0.02). After additional adjustment for diabetes at baseline, the risk associated with HDL-C CIII+ was 1.14 (0.94-1.39).

FIG. 1 shows the risk of CHD according to quintiles of total HDL-C, and HDL-C with and without apoCIII in the combined study sample based on the fully adjusted models. Compared to the lowest quintile, the RR in the top quintile for HDL-C CIII$^+$ was 1.35 (0.81-2.22), for HDL-C CIII$^-$ it was 0.32 (0.17-0.59), and for total HDL-C it was 0.47 (0.28-0.79).

Concentration of apoCIII and risk of coronary heart disease: The concentration of apoCIII in HDL tended for a direct association with risk of CHD that was not statistically significant. The RR per SD (9.03 mg/dl) was 1.14 (0.95-1.36) (Table 4).

The controversies in establishing the role of HDL in atherosclerosis may be due in part to the lack of specificity in the measurements of HDL-C. In a prospective study of generally healthy middle-aged men and women, we found that HDL is composed of two populations having opposite associations with CHD. The major HDL-C type lacking apoC-III has the expected protective association with CHD but stronger than that seen for the total HDL-C. The minor HDL-C type defined by its having apoC-III directly predicts incidence of CHD suggesting an adverse effect on atherosclerosis.

Our study extends that of others where different methods for HDL sub-classification have been investigated. In previous studies using various techniques for measurement of HDL particle size, it has been suggested that often,[14,17] but not always,[16] the largest HDL particles are most strongly inversely associated with risk of CHD. Recently, the large WHS reported that use of proton nuclear magnetic resonance spectroscopy measures to capture HDL particle size and number did not add to the information gained by traditional lipid measures. However, they observed that a high concentration the smallest HDL particles was associated with an elevated risk of CVD, although the test for tend was not statistically significant.[17] Other more experimental subclassifications include the effect of HDL on cholesterol efflux or anti-inflammatory indices of HDL.[18] These new experimental assays are of scientific interest and suggests that the measure of total HDL-C may be diluted due to a mixing of cholesterol distributed in both anti- and pro-atherogenic HDL particles. However, so far, the concept and understanding of what makes a dysfunctional or even pro-inflammatory HDL subtype remains elusive.[12] Our data suggest that level of HDL-C with apoCIII was not inversely associated with the risk of CHD, supporting the hypothesis that apoCIII may play an important role for the metabolic properties of the HDL particle. Consistent with our findings, it has previously been shown that levels of total apoCIII and apoCIII in HDL were directly associated with risk of CHD, but that these associations are not robust to multivariable adjustments for important cardiovascular risk factors.[23,29,30] These data may suggest that apoCIII acts as a modifier of the functional properties of the HDL particles, making the HDL particle dysfunctional, rather than having direct atherogenic effects in itself. Kawakami et al. reported that HDL without apoCIII, but not HDL with apoCIII, limits the pro-inflammatory adhesion of human monocytes to endothelial cells.[21] Other possible explanations for our results include inhibition of HDL particle maturation by apoCIII or inhibition of the catabolism of cholesterol in HDL, as also suggested by the known inhibiting action of apoCIII on hepatic lipase. ApoCIII also plays an important role in the catabolism of triglycerides through the inhibition of lipolysis by lipoprotein lipase. Although we explored additional adjustments for atherogenic apoB-containing lipoproteins in our multivariable models, we cannot exclude the potential for residual effects caused by the modest positive correlation between HDL-C CIII$^+$ and triglycerides (0.17).

It is among our study limitations, that we only had one assessment of the lipid subfractions. Thus, our findings cannot determine whether changes in the proportions of cholesterol transported in HDL particles with and without apoCIII are causally related to risk of CHD. Because undiagnosed illness at baseline might create a spurious association, we compared the associations from analyses in strata of 5 years of follow-up. The results were similar to those presented here both when cases that occurred during the first five and subsequent years of follow-up were considered (data not shown).

In conclusion, we found that HDL-C with and without apoCIII showed opposite associations with the risk of CHD in a prospective study of apparently healthy men and women. This highlights the need to recognize that HDL comprises a group of particles that are structurally and functionally diverse and that subpopulations may be more or less closely linked with atherosclerosis.[11] We believe that presence of apoCIII on HDL is a useful marker of a dysfunctional form of HDL-C without cardioprotective benefits. Measurement of the proportions of HDL with and without apoCIII has implications for future risk discrimination and in the assessment of response to novel therapeutic interventions.

TABLE 1

Characteristics of women and men in whom CHD developed during follow-up and matched controls in the Nurses' Health Study (NHS) and the Health Professionals Follow-Up Study (HPFS).*

| | NHS | | HPFS | |
|---|---|---|---|---|
| Variable | Cases (n = 284) | Controls (n = 284) | Cases (n = 348) | Controls (n = 349) |
| Age (yrs) | 60.2 ± 6.5 | 60.3 ± 6.4 | 64.4 ± 8.5 | 64.2 ± 8.5 |
| BMI (kg/m$^2$) | 26.7 ± 5.7 | 25.2 ± 4.1 | 26.1 ± 3.3 | 25.5 ± 3.5 |
| Current smoker | 26.8% | 26.1% | 8.3% | 7.7% |
| Alcohol (g/d) | 4.3 ± 8.1 | 5.6 ± 9.5 | 10.6 ± 15.5 | 12.6 ± 15.5 |
| Physical activity (METhr/wk) | 17.8 ± 21.0 | 20.1 ± 21.4 | 35.0 ± 36.5 | 37.0 ± 38.1 |
| Caucasian ethnicity | 81.4% | 82.7% | 93.7% | 94.2% |
| Postmenopausal | 87.1% | 84.9% | N/A | N/A |
| Family history of MI | 20.4% | 14.1% | 41.9% | 34.6% |
| Diabetes† | 15.5% | 6.0% | 8.1% | 3.7% |
| Hypercholesterolemia† | 54.2% | 41.6% | 47.7% | 39.3% |
| Hypertension† | 53.5% | 31.7% | 36.8% | 28.9% |
| Lipid concentrations (mg/dl) | | | | |
| Total cholesterol | 234 ± 46.1 | 230 ± 46.9 | 218 ± 40.1 | 210 ± 36.9 |
| Triglycerides | 136 ± 94.9 | 108 ± 57.2 | 140 ± 80.9 | 114 ± 70.1 |
| LDL-C | 147 ± 40.8 | 143 ± 40.6 | 135 ± 33.9 | 126 ± 32.0 |
| HDL-C | 67.9 ± 21.7 | 72.1 ± 24.0 | 46.6 ± 16.5 | 48.9 ± 15.5 |
| HDL-C CIII$^-$ | 58.3 ± 20.1 | 62.7 ± 22.6 | 41.2 ± 15.2 | 43.6 ± 14.1 |

TABLE 1-continued

Characteristics of women and men in whom CHD developed during follow-up and matched controls in the Nurses' Health Study (NHS) and the Health Professionals Follow-Up Study (HPFS).*

|  | NHS | | HPFS | |
|---|---|---|---|---|
| Variable | Cases (n = 284) | Controls (n = 284) | Cases (n = 348) | Controls (n = 349) |
| HDL-C CIII+ | 9.53 ± 4.30 | 9.31 ± 3.87 | 5.43 ± 2.52 | 5.38 ± 2.56 |
| % HDL-C with CIII | 14.8 ± 7.51 | 14.7 ± 8.14 | 11.9 ± 4.43 | 11.1 ± 3.94 |
| apoCIII in HDL | 12.2 ± 10.3 | 11.7 ± 7.29 | 12.1 ± 9.67 | 11.4 ± 8.05 |

*Matching criteria were: age, smoking and date of blood sampling. Values are means ± standard deviation of continuous covariates or percentages. Fasting at blood draw: HPFS = 65%, NHS = 79%.

†Self-reported diagnosis before blood draw.

‡Diagnosed with hypercholesterolemia or reporting to use cholesterol-lowering medication.

TABLE 2

Age-standardized mean values of characteristics and p for test of trend according to quintiles of HDL-C with (CIII+) and without (CIII−) apoCIII in the Nurses' Health Study (NHS), and the Health Professionals Follow Up Study (HPFS).

|  | NHS | | | | | | HPFS | | | | | |
|---|---|---|---|---|---|---|---|---|---|---|---|---|
|  | Q1 | Q2 | Q3 | Q4 | Q5 | p | Q1 | Q2 | Q3 | Q4 | Q5 | p |
| HDL-C CIII− | 33.3 | 50.5 | 61.5 | 73.6 | 96.7 |  | 25.6 | 35.1 | 42.1 | 49.6 | 65.3 |  |
| BMI (kg/m²) | 27.0 | 26.9 | 25.6 | 25.9 | 23.9 | 0.001 | 26.5 | 26.2 | 25.6 | 25.7 | 24.8 | 0.001 |
| Alcohol (g/d) | 3.38 | 4.30 | 4.63 | 5.43 | 6.65 | 0.01 | 9.24 | 8.86 | 12.2 | 12.1 | 16.3 | 0.001 |
| Physical activity (METhrs/wk) | 16.5 | 16.7 | 22.9 | 18.3 | 21.8 | 0.06 | 30.8 | 41.7 | 35.8 | 35.5 | 43.9 | 0.04 |
| Current smoker (%) | 36 | 21 | 22 | 26 | 27 | 0.32 | 11 | 8 | 5 | 7 | 8 | 0.20 |
| Postmenopausal | 84 | 89 | 87 | 85 | 83 | 0.32 | na | na | na | na | na |  |
| Diabetes (%) | 14 | 16 | 7 | 10 | 4 | 0.003 | 8 | 11 | 4 | 4 | 3 | 0.01 |
| Hypertension (%) | 54 | 43 | 43 | 36 | 36 | 0.003 | 36 | 34 | 33 | 34 | 27 | 0.18 |
| Nutrients (% energy) |  |  |  |  |  |  |  |  |  |  |  |  |
| Total fat | 32.1 | 31.2 | 31.3 | 31.3 | 30.9 | 0.18 | 31.5 | 30.8 | 29.3 | 30.1 | 30.4 | 0.14 |
| Mono unsaturated fat | 12.2 | 12.0 | 12.0 | 12.0 | 11.9 | 0.27 | 12.5 | 12.3 | 11.6 | 11.9 | 12.1 | 0.65 |
| Poly unsaturated fat | 5.84 | 5.86 | 6.10 | 5.92 | 5.92 | 0.61 | 5.71 | 5.61 | 5.31 | 5.40 | 5.52 | 0.16 |
| Saturated fat | 11.2 | 10.5 | 10.5 | 10.6 | 10.4 | 0.06 | 10.4 | 10.0 | 11.6 | 11.9 | 12.1 | 0.22 |
| Transunsaturated fat | 1.55 | 1.50 | 1.55 | 1.52 | 1.44 | 0.25 | 1.44 | 1.33 | 1.33 | 1.33 | 1.37 | 0.43 |
| Carbohydrate | 49.9 | 50.6 | 50.8 | 50.4 | 49.9 | 0.99 | 50.7 | 51.0 | 51.8 | 50.7 | 49.2 | 0.001 |
| Protein | 19.1 | 19.0 | 18.6 | 18.8 | 18.9 | 0.53 | 17.2 | 17.7 | 17.2 | 17.4 | 17.3 | 0.14 |
| Biomarkers (mg/dl) |  |  |  |  |  |  |  |  |  |  |  |  |
| Total HDL-C | 41.9 | 59.0 | 70.7 | 83.4 | 108.7 | 0.001 | 29.6 | 40.0 | 47.8 | 55.5 | 72.4 | 0.001 |
| HDL-CCIII+ | 8.61 | 8.51 | 9.19 | 9.82 | 12.0 | 0.001 | 3.94 | 4.91 | 5.63 | 5.87 | 7.08 | 0.001 |
| ApoCIII in HDL | 10.4 | 11.2 | 12.5 | 12.2 | 14.1 | 0.003 | 11.2 | 11.1 | 11.7 | 13.1 | 12.1 | 0.001 |
| Cholesterol | 212.0 | 218.7 | 243.7 | 240.6 | 256.9 | 0.001 | 200.3 | 204.6 | 218.8 | 220.0 | 228.6 | 0.001 |
| LDL-C | 151.7 | 140.3 | 154.7 | 143.0 | 135.2 | 0.04 | 126.1 | 127.5 | 135.1 | 132.1 | 133.3 | 0.03 |
| Triglycerides | 124.5 | 146.0 | 125.3 | 107.9 | 100.1 | 0.001 | 128.8 | 132.0 | 137.9 | 122.7 | 107.6 | 0.001 |
| CRP | 0.43 | 0.49 | 0.43 | 0.43 | 0.36 | 0.37 | 2.99 | 2.30 | 2.45 | 2.97 | 1.86 | 0.25 |
| HDL-C CIII+ | 4.46 | 6.87 | 8.91 | 11.1 | 15.7 |  | 2.60 | 3.97 | 4.92 | 6.13 | 9.15 |  |
| BMI (kg/m²) | 26.3 | 26.2 | 25.5 | 26.1 | 25.9 | 0.49 | 25.8 | 25.8 | 26.0 | 25.8 | 25.7 | 0.83 |
| Alcohol (g/d) | 3.73 | 5.58 | 5.03 | 4.98 | 4.66 | 0.60 | 8.38 | 9.23 | 11.9 | 10.3 | 17.5 | 0.001 |
| Physical activity (METhrs/wk) | 17.0 | 20.2 | 21.3 | 16.9 | 19.4 | 0.77 | 37.3 | 34.4 | 38.3 | 34.2 | 39.6 | 0.65 |
| Current smoker (%) | 26 | 26 | 30 | 29 | 22 | 0.68 | 10 | 6 | 5 | 7 | 11 | 0.89 |
| Postmenopausal | 88 | 84 | 89 | 85 | 84 | 0.44 | na | na | na | na | na |  |
| Diabetes (%) | 12 | 7 | 7 | 10 | 16 | 0.22 | 6 | 5 | 5 | 4 | 10 | 0.25 |
| Hypertension (%) | 42 | 50 | 36 | 43 | 48 | 0.57 | 29 | 34 | 26 | 32 | 42 | 0.05 |
| Nutrients (% energy) |  |  |  |  |  |  |  |  |  |  |  |  |
| Total fat | 30.6 | 31.8 | 31.4 | 31.7 | 31.5 | 0.28 | 30.6 | 29.7 | 31.1 | 30.6 | 30.3 | 0.89 |
| Monounsaturated fat | 11.6 | 12.2 | 12.1 | 12.2 | 12.2 | 0.22 | 12.0 | 11.8 | 12.4 | 12.0 | 12.1 | 0.64 |
| Polyunsaturated fat | 5.93 | 5.90 | 5.97 | 5.68 | 6.05 | 0.89 | 5.60 | 5.48 | 5.51 | 5.57 | 5.41 | 0.61 |
| Saturated fat | 10.3 | 10.9 | 10.6 | 11.0 | 6.07 | 0.32 | 10.2 | 9.64 | 10.3 | 10.1 | 9.98 | 0.84 |
| Transunsaturated fat | 1.51 | 1.62 | 1.43 | 1.52 | 1.50 | 0.44 | 1.36 | 1.37 | 1.41 | 1.37 | 1.31 | 0.51 |
| Carbohydrate | 52.2 | 49.5 | 50.0 | 49.4 | 50.4 | 0.11 | 52.1 | 52.6 | 50.1 | 50.8 | 48.5 | 0.001 |
| Protein | 18.5 | 18.9 | 19.0 | 19.2 | 18.8 | 0.27 | 17.1 | 17.2 | 17.1 | 17.8 | 17.4 | 0.14 |

TABLE 2-continued

Age-standardized mean values of characteristics and p for test of trend according to quintiles of HDL-C with (CIII⁺) and without (CIII⁻) apoCIII in the Nurses' Health Study (NHS), and the Health Professionals Follow Up Study (HPFS).

|  | NHS | | | | | | HPFS | | | | | |
|---|---|---|---|---|---|---|---|---|---|---|---|---|
|  | Q1 | Q2 | Q3 | Q4 | Q5 | p | Q1 | Q2 | Q3 | Q4 | Q5 | p |
| Biomarkers (mg/dl) | | | | | | | | | | | | |
| Total HDL-C | 57.1 | 62.3 | 70.9 | 74.8 | 86.2 | 0.001 | 34.7 | 43.1 | 47.3 | 51.7 | 60.8 | 0.001 |
| HDL-C CIII⁻ | 52.4 | 55.2 | 61.8 | 63.7 | 70.4 | 0.001 | 32.1 | 39.2 | 42.4 | 45.6 | 51.7 | 0.001 |
| ApoCIII in HDL | 8.83 | 10.5 | 13.2 | 12.0 | 15.3 | 0.001 | 9.25 | 9.42 | 10.8 | 11.6 | 17.2 | 0.001 |
| Cholesterol | 215.0 | 218.0 | 239.1 | 237.9 | 251.5 | 0.001 | 195.4 | 205.3 | 219.9 | 220.8 | 227.5 | 0.001 |
| LDL-C | 143.2 | 141.1 | 150.9 | 145.7 | 145.5 | 0.45 | 123.6 | 129.0 | 138.4 | 133.5 | 131.1 | 0.04 |
| Triglycerides | 101.0 | 110.4 | 123.4 | 122.7 | 152.0 | 0.001 | 107.6 | 115.7 | 118.0 | 137.6 | 154.9 | 0.001 |
| CRP | 0.45 | 0.34 | 0.47 | 0.41 | 0.47 | 0.63 | 2.66 | 2.72 | 1.58 | 2.78 | 3.09 | 0.50 |

TABLE 3

Incidence rate ratios (IRR) and 95% confidence intervals for CHD per SD of total HDL-C, HDL-C with (CIII⁺) and without (CIII⁻) apoCIII in the Nurses' Health Study (NHS), and the Health Professionals Follow Up Study (HPFS).*

|  | NHS | | HPFS | | ALL | |
|---|---|---|---|---|---|---|
| HDL variable (1 SD) | IRR | P trend | IRR | P trend | IRR | P trend |
| Total HDL-C (22.8 mg/dL) | | | | | | |
| Unadjusted | 0.69 (0.55-0.87) | 0.002 | 0.71 (0.52-0.95) | 0.02 | 0.71 (0.58-0.85) | 0.0002 |
| Multivariable adjusted | 0.75 (0.58-0.98) | 0.03 | 0.78 (0.57-1.08) | 0.14 | 0.76 (0.62-0.92) | 0.006 |
| +LDL and triglycerides | 0.78 (0.60-1.02) | 0.07 | 0.79 (0.56-1.12) | 0.18 | 0.79 (0.64-0.97) | 0.02 |
| +diabetes | 0.77 (0.58-1.01) | 0.06 | 0.80 (0.57-1.13) | 0.21 | 0.79 (0.64-0.97) | 0.03 |
| HDL-C CIII⁻ (20.7 mg/dL) | | | | | | |
| Unadjusted† | 0.53 (0.40-0.70) | <0.0001 | 0.62 (0.44-0.86) | 0.004 | 0.56 (0.45-0.70) | <0.0001 |
| Multivariable adjusted | 0.58 (0.42-0.80) | 0.0008 | 0.70 (0.49-0.99) | 0.04 | 0.63 (0.50-0.79) | <0.0001 |
| +LDL and triglycerides | 0.57 (0.40-0.81) | 0.001 | 0.77 (0.53-1.13) | 0.18 | 0.66 (0.52-0.85) | 0.001 |
| +diabetes | 0.61 (0.43-0.87) | 0.007 | 0.80 (0.54-1.18) | 0.26 | 0.70 (0.54-0.90) | 0.005 |
| HDL-C CIII⁺ (3.76 mg/dL) | | | | | | |
| Unadjusted† | 1.36 (1.09-1.70) | 0.007 | 1.24 (0.93-1.66) | 0.14 | 1.31 (1.10-1.56) | 0.003 |
| Multivariable adjusted | 1.31 (1.04-1.66) | 0.02 | 1.21 (0.90-1.64) | 0.21 | 1.27 (1.06-1.52) | 0.01 |
| +LDL and triglycerides | 1.37 (1.06-1.76) | 0.02 | 1.03 (0.74-1.44) | 0.85 | 1.22 (1.00-1.47) | 0.05 |
| +diabetes | 1.24 (0.96-1.61) | 0.11 | 1.00 (0.71-1.40) | 0.99 | 1.14 (0.94-1.39) | 0.18 |

Incidence rate ratios (IRR) obtained from conditional logistic regression models. Multivariable model includes: alcohol, BMI, family history of MI before age 60 and hypertension. Information on hypertension and diabetes were based on self-reports at time of blood draw.
†HDL-C with and without CIII simultaneously included in all models.

TABLE 4

Incidence rate ratios (IRR) and 95% confidence intervals for CHD according to quintiles and per SD of apoCIII in HDL in the Nurses' Health Study (NHS), and the Health Professionals Follow Up Study (HPFS).*

|  | Quintiles of apoCIII in HDL | | | | | Per SD | |
|---|---|---|---|---|---|---|---|
|  | Q1 | Q2 | Q3 | Q4 | Q5 | (9.03 mg/dL) | P trend |
| Median | 3.69 | 6.87 | 9.84 | 13.5 | 23.5 | | |
| Cases | 128 | 130 | 101 | 140 | 131 | | |
| Unadjusted | 1.0 (ref) | 1.03 (0.70-1.52) | 0.82 (0.53-1.26) | 1.08 (0.70-1.68) | 1.04 (0.62-1.73) | 1.16 (0.98-1.37) | 0.09 |
| Multivariable adjusted | 1.0 (ref) | 1.22 (0.81-1.84) | 0.94 (0.59-1.50) | 1.24 (0.77-2.00) | 1.37 (0.77-2.44) | 1.14 (0.95-1.36) | 0.16 |
| +LDL and triglycerides | 1.0 (ref) | 1.08 (0.71-1.66) | 0.83 (0.51-1.34) | 1.05 (0.63-1.74) | 1.13 (0.61-2.09) | 1.07 (0.89-1.29) | 0.48 |
| +diabetes | 1.0 (ref) | 1.01 (0.65-1.56) | 0.78 (0.48-1.28) | 0.97 (0.58-1.62) | 1.04 (0.56-1.94) | 1.06 (0.87-1.28) | 0.58 |

*Incidence rate ratios (IRR) obtained from conditional logistic regression models. Multivariable model includes: alcohol, BMI, family history of MI before age 60, hypertension and total HDL-C. Information on hypertension and diabetes were based on self-reports at time of blood draw

References

1. Gordon T, Castelli W P, Hjortland M C, Kannel W B, Dawber T R. High density lipoprotein as a protective factor against coronary heart disease. The Framingham Study. Am J Med 1977; 62:707-714.
2. Sharrett A R, Ballantyne C M, Coady S A et al. Coronary heart disease protection from lipoprotein cholesterol levels, triglycerides, lipoprotein(a), apolipoproteins A-I and B, and HDL density subfractions: The Atherosclerosis Risk in Communities (ARIC) Study. Circulation 2002; 104:1108-1113.
3. Assmann G, Schulte H, von E A, Huang Y. High-density lipoprotein cholesterol as a predictor of coronary heart disease risk. The PROCAM experience and pathophysiological implications for reverse cholesterol transport. Atherosclerosis 1996; 124 Suppl:S11-S20.
4. Grundy S M, Cleeman J I, Merz C N et al. Implications of recent clinical trials for the National Cholesterol Education Program Adult Treatment Panel III Guidelines. J Am Coll Cardiol 2004; 44(3):720-732.
5. Singh I M, Shishehbor M H, Ansell B J. High-density lipoprotein as a therapeutic target: a systematic review. JAMA 2007; 298(7):786-798.
6. Assmann G, Gotto A M, Jr. HDL cholesterol and protective factors in atherosclerosis. Circulation 2004; 109(23 Suppl 1):1118-14.
7. Nissen S E, Tardif J C, Nicholls S J et al. Effect of torcetrapib on the progression of coronary atherosclerosis. N Engl J Med 2007; 356(13):1304-1316.
8. Barter P J, Caulfield M, Eriksson M et al. Effects of torcetrapib in patients at high risk for coronary events. N Engl J Med 2007; 357(21):2109-2122.
9. Briel M, Ferreira-Gonzalez I, You J J et al. Association between change in high density lipoprotein cholesterol and cardiovascular disease morbidity and mortality: systematic review and meta-regression analysis. BMJ 2009; 338:b92.
10. Davidson W S, Silva R A, Chantepie S, Lagor W R, Chapman M J, Kontush A. Proteomic analysis of defined HDL subpopulations reveals particle-specific protein clusters: relevance to antioxidative function. Arterioscler Thromb Vasc Biol 2009; 29(6):870-876.
11. Vaisar T, Pennathur S, Green P S et al. Shotgun proteomics implicates protease inhibition and complement activation in the antiinflammatory properties of HDL. J Clin Invest 2007; 117(3):746-756.
12. Movva R, Rader D J. Laboratory assessment of HDL heterogeneity and function. Clin Chem 2008; 54(5):788-800.
13. Stampfer M J, Sacks F M, Salvini S, Willett W C, Hennekens C H. A prospective study of cholesterol, apolipoproteins, and the risk of myocardial infarction. N Engl J Med 1991; 325:373-381.
14. Asztalos B F, Collins D, Cupples L A et al. Value of high-density lipoprotein (HDL) subpopulations in predicting recurrent cardiovascular events in the Veterans Affairs HDL Intervention Trial. Arterioscler Thromb Vasc Biol 2005; 25(10):2185-2191.
15. El H K, Arsenault B J, Franssen R et al. High-density lipoprotein particle size and concentration and coronary risk. Ann Intern Med 2009; 150(2):84-93.
16. van der Steeg W A, Holme I, Boekholdt S M et al. High-density lipoprotein cholesterol, high-density lipoprotein particle size, and apolipoprotein A-I: significance for cardiovascular risk: the IDEAL and EPIC-Norfolk studies. J Am Coll Cardiol 2008; 51(6):634-642.
17. Mora S, Otvos J D, Rifai N, Rosenson R S, Buring J E, Ridker P M. Lipoprotein particle profiles by nuclear magnetic resonance compared with standard lipids and apolipoproteins in predicting incident cardiovascular disease in women. Circulation 2009; 119(7):931-939.
18. Ansell B J, Navab M, Hama S et al. Inflammatory/antiinflammatory properties of high-density lipoprotein distinguish patients from control subjects better than high-density lipoprotein cholesterol levels and are favorably affected by simvastatin treatment. Circulation 2003; 108(22):2751-2756.
19. Ginsberg H N, Le N A, Goldberg I J et al. Apolipoprotein B metabolism in subjects with deficiency of apolipoproteins CIII and AI. Evidence that apolipoprotein CIII inhibits catabolism of triglyceride-rich lipoproteins by lipoprotein lipase in vivo. J Clin Invest 1986; 78(5):1287-1295.
20. Kawakami A, Aikawa M, Alcaide P, Luscinskas F W, Libby P, Sacks F M. Apolipoprotein CIII induces expression of vascular cell adhesion molecule-1 in vascular endothelial cells and increases adhesion of monocytic cells. Circulation 2006; 114(7):681-687.
21. Kawakami A, Aikawa M, Libby P, Alcaide P, Luscinskas F W, Sacks F M. Apolipoprotein CIII in apolipoprotein B lipoproteins enhances the adhesion of human monocytic cells to endothelial cells. Circulation 2006; 113(5):691-700.
22. Kawakami A, Osaka M, Tani M et al. Apolipoprotein CIII links hyperlipidemia with vascular endothelial cell dysfunction. Circulation 2008; 118(7):731-742.
23. Sacks F M, Alaupovic P, Moye L E et al. VLDL, apolipoproteins B, CIII, and E, and risk of recurrent coronary events in the Cholesterol and Recurrent Events (CARE) Trial. Circulation 2000; 102:1886-1892.
24. Lee S J, Campos H, Moye L A, Sacks F M. LDL containing apolipoprotein CIII is an independent risk factor for coronary events in diabetic patients. Arterioscler Thromb Vasc Biol 2003; 23(5):853-858.
25. Colditz G A, Manson J E, Hankinson S E. The Nurses' Health Study: 20-year contribution to the understanding of health among women. J Womens Health 1997; 6(1):49-62.
26. Rimm E B, Giovannucci E L, Stampfer M J, Colditz G A, Litin L B, Willett W C. Reproducibility and validity of a expanded self-administered semiquantitative food frequency questionnaire among male health professionals. Am J Epidemiol 1992; 135:1114-1126.
27. Prentice R L, Breslow N E. Retrospective studies and failure time models. Biometrika 1978; 65:153-158.
28. Furtado J D, Campos H, Appel L J et al. Effect of protein, unsaturated fat, and carbohydrate intakes on plasma apolipoprotein B and VLDL and LDL containing apolipoprotein C-III: results from the OmniHeart Trial. Am J Clin Nutr 2008; 87(6):1623-1630.
29. Blankenhorn D H, Alaupovic P, Wickam E, Chin H P, Azen S P. Prediction of angiographic change in native human coronary arteries and aortocoronary bypass grafts. Circulation 1990; 81:470-476.
30. Onat A, Hergenc G, Sansoy V et al. Apolipoprotein C-III, a strong discriminant of coronary risk in men and a determinant of the metabolic syndrome in both genders. Atherosclerosis 2003; 168(1):81-89.

We claim:
1. A method of characterizing an individual's risk of developing coronary heart disease or having a cardiovascular event, the method comprising:

(i) measuring a level of high density lipoprotein cholesterol apoCIII (HDL-C apoCIII) and a level of C-reactive protein (CRP) in a blood plasma sample obtained from the individual;
(ii) comparing the level of HDL-C apoCIII in the blood plasma sample to a predetermined value for HDL-C apoCIII and comparing the level of CRP in the blood plasma sample to a predetermined value for CRP; and
(iii) identifying the individual as at increased risk of developing coronary heart disease or of having a cardiovascular event if the level of HDL-C apoCIII in the blood plasma sample is at or above the predetermined value for HDL-C apoCIII and if the level of CRP in the blood plasma sample is at or above the predetermined value for CRP, or identifying the individual as at decreased risk of developing coronary heart disease or of having a cardiovascular event if the level of HDL-C apoCIII in the blood plasma sample is below the predetermined value for HDL-C apoCIII and if the level of CRP in the blood plasma sample is below the predetermined value for CRP, wherein the cardiovascular event is myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

2. The method of claim 1, wherein the individual has a normal or below normal total blood plasma level of apoCIII.

3. The method of claim 1, wherein the individual has a normal or above normal total blood plasma level of HDL-C.

4. The method of claim 1, wherein the individual has a normal or below normal total blood plasma level apoCIII and a normal or above normal total blood plasma level HDL-C.

5. The method of claim 1, wherein the predetermined value for HDL-C apoCIII is an HDL-C apoCIII total blood plasma level of about 2 mg/dl.

6. The method of claim 1, wherein the cardiovascular event is myocardial infarction or stroke.

7. The method of claim 1, wherein the method further comprises:
(iv) administering an agent useful for decreasing the risk of coronary heart disease or a cardiovascular event to an individual identified as at increased risk of developing coronary heart disease or having a cardiovascular event.

8. A method of characterizing an individual's risk of developing coronary heart disease or having a cardiovascular event, the method comprising:
(i) measuring a level of high density lipoprotein cholesterol apoCIII (HDL-C apoCIII) and a level of total cholesterol in a blood plasma sample obtained from the individual;
(ii) comparing the level of HDL-C apoCIII in the blood plasma sample to a predetermined value for HDL-C apoCIII and comparing the level of total cholesterol in the blood plasma sample to a predetermined value for total cholesterol; and
(iii) identifying the individual as at increased risk of developing coronary heart disease or of having a cardiovascular event if the level of HDL-C apoCIII in the blood plasma sample is at or above the predetermined value for HDL-C apoCIII and a level of total cholesterol in the blood plasma sample is at or above the predetermined value for total cholesterol, or identifying the individual as at decreased risk of developing coronary heart disease or of having a cardiovascular event if the level of HDL-C apoCIII in the blood plasma sample is below the predetermined value for HDL-C apoCIII and a level of total cholesterol in the blood plasma sample is below the predetermined value for total cholesterol, wherein the cardiovascular event is myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

9. The method of claim 8, wherein the individual has a normal or below normal total blood plasma level of apoCIII.

10. The method of claim 8, wherein the individual has a normal or above normal total blood plasma level of HDL-C.

11. The method of claim 8, wherein the individual has a normal or below normal total blood plasma level apoCIII and a normal or above normal total blood plasma level HDL-C.

12. The method of claim 8, wherein the predetermined value for HDL-C apoCIII is an HDL-C apoCIII total blood plasma level of about 2 mg/dl.

13. The method of claim 8, wherein the cardiovascular event is myocardial infarction or stroke.

14. The method of claim 8, wherein the method further comprises:
(iv) administering an agent useful for decreasing the risk of coronary heart disease or a cardiovascular event to an individual identified as at increased risk of developing coronary heart disease or having a cardiovascular event.

15. A method of characterizing an individual's risk of developing coronary heart disease or having a cardiovascular event, the method comprising:
(i) performing an enzyme-linked immunoabsorbent assay (ELISA) assay to measure a level of high density lipoprotein cholesterol apoCIII (HDL-C apoCIII) in a blood plasma sample obtained from the individual;
(ii) comparing the level of HDL-C apoCIII in the sample to a predetermined value; and
(iii) identifying the individual as at increased risk of developing coronary heart disease or of having a cardiovascular event if the level of HDL-C apoCIII in the sample is at or above the predetermined value, or identifying the individual as at decreased risk of developing coronary heart disease or of having a cardiovascular event if the level of HDL-C apoCIII in the sample is below the predetermined value, wherein the cardiovascular event is myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

16. The method of claim 15, wherein the individual has a normal or below normal total blood plasma level of apoCIII.

17. The method of claim 15, wherein the individual has a normal or above normal total blood plasma level of HDL-C.

18. The method of claim 15, wherein the individual has a normal or below normal total blood plasma level apoCIII and a normal or above normal total blood plasma level HDL-C.

19. The method of claim 15, wherein the predetermined value is an HDL-C apoCIII total blood plasma level of about 2 mg/dl.

20. The method of claim 15, wherein the cardiovascular event is myocardial infarction or stroke.

* * * * *

UNITED STATES PATENT AND TRADEMARK OFFICE
CERTIFICATE OF CORRECTION

| | | |
|---|---|---|
| PATENT NO. | : 8,846,321 B2 | Page 1 of 1 |
| APPLICATION NO. | : 13/046682 | |
| DATED | : September 30, 2014 | |
| INVENTOR(S) | : Frank M. Sacks et al. | |

It is certified that error appears in the above-identified patent and that said Letters Patent is hereby corrected as shown below:

In the Specification

Please replace the paragraph at Column 1, Lines 14-17 with the following paragraph:
--This invention was made with Government support under grant HL070159, AA011181, HL034594, and HL035464 awarded by the National Institutes of Health (NIH). The Government has certain rights to this invention.--

Signed and Sealed this
Twelfth Day of May, 2020

Andrei Iancu
*Director of the United States Patent and Trademark Office*